United States Patent [19]
Tan et al.

[11] Patent Number: 5,616,765
[45] Date of Patent: Apr. 1, 1997

[54] METHOD FOR THE PREPARATION OF 4-HYDROXY-AND 4-TRIMETHYLSILOXYBENZOCYCLOBUTENE

[75] Inventors: Loon-Seng Tan, Centerville; Narayanan Venkatasubramanian, Fairborn, both of Ohio

[73] Assignee: The United States of America as represented by the Secretary of the Air Force, Washington, D.C.

[21] Appl. No.: 605,242

[22] Filed: Feb. 12, 1996

[51] Int. Cl.$^6$ .................. C07F 7/08; C07F 7/18
[52] U.S. Cl. ........................... 556/486; 568/734
[58] Field of Search .............. 556/486; 568/734

[56] References Cited

U.S. PATENT DOCUMENTS

| | | |
|---|---|---|
| 4,540,763 | 9/1985 | Kirchoff . |
| 4,642,329 | 2/1987 | Kirchoff et al. . |
| 4,724,260 | 2/1988 | Kirchoff et al. . |
| 4,743,399 | 5/1988 | Kirchoff et al. . |
| 4,812,588 | 3/1989 | Schrock . |
| 4,831,172 | 5/1989 | Hahn et al. . |
| 4,916,248 | 4/1990 | Brownell et al. ............... 556/486 |
| 4,985,576 | 1/1991 | Rohrmann et al. ............ 556/486 X |
| 4,999,449 | 3/1991 | Kirchoff . |
| 5,247,037 | 9/1993 | Kirchoff et al. . |
| 5,514,827 | 5/1996 | Petty ............................... 556/486 X |

FOREIGN PATENT DOCUMENTS

515170A2   11/1992   European Pat. Off. .

OTHER PUBLICATIONS

L-S Tan, N. Venkatasubramanian, M.D. Houtz and C.L. Brenner, "Thermosetting Matrix Resins Based On 4-Hydroxybenzocyclobutene", Polymer Preprints, vol. 36, No. 1, Apr. 1995, published Mar. 1, 1995, pp. 443–444.

*Primary Examiner*—Paul F. Shaver
*Attorney, Agent, or Firm*—Charles E. Bricker; Thomas L. Kundert

[57] ABSTRACT

4-Hydroxybenzocyclobutene is prepared by the demethylation of 4-methoxybenzocyclobutene in the presence of aluminum iodide. A new compound 4-trimethylsiloxybenzocyclobutene is prepared by reacting 4-hydroxybenzocyclobutene with chlorotrimethylsilane.

3 Claims, No Drawings

METHOD FOR THE PREPARATION OF 4-HYDROXY-AND 4-TRIMETHYLSILOXYBENZOCYCLOBUTENE

RIGHTS OF THE GOVERNMENT

The invention described herein may be manufactured and used by or for the Government of the United States for all governmental purposes without the payment of any royalty.

BACKGROUND OF THE INVENTION

This invention relates to methods for the preparation of 4-hydroxy-and 4-trimethylsiloxy-benzocyclobutene.

Benzocyclobutene (BCB)-based polymeric materials have recently attracted growing attention and research interest in the area of structural and electronic applications because of the versatile chemistry of benzocyclobutene as well as the combined advantages of processability and properties. The cure chemistry of benzocyclobutene is based upon the propensity of the four-membered ring to undergo electrocyclic ring-opening at elevated temperatures (~200° C.) to provide reactive o-quinodimethane that will undergo dimerization and polymerization, or react with an attendant dienophile to form a Dieis-Alder adduct.

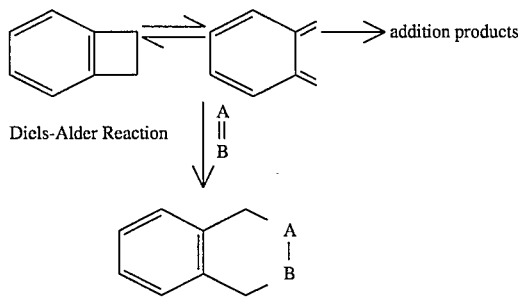

Research reports describing the synthesis and characterization of high-temperature BCB-based materials for potential structural and aerospace applications have appeared. These heat-resistant thermosets include, for example, homopolymerized bisbenzocyclobutene-terminated imide monomers and a variety of resins generated from Dieis-Alder reactions of bisbenzocyclobutene-terminated imide monomers with monomers containing dienophilic endgroups such as acetylene, phenylacetylene and maleimide. Recently, the incorporation of the thermally reactive benzocyclobutene into the main chain of polymeric materials for lateral crosslinking has also been reported. The objective was to improve the compressive strength of high modulus fibers such as Kevlar® via the use of a latently crosslinkable monomer, 1,2-dihydrocyclobutabenzene 3,6-dicarboxylic acid.

4-Aminobenzocyclobutene (4-AMBCB) is a simple, polymerizable endcapping agent that has been used for the preparation of bis(benzocyclobutene) (BBCB)-terminated monomers for heat-resistant, thermosetting polyimides. Another simple BCB-endcapping agent bearing a nucleophilic center is 4-hydroxybenzocyclobutene (4-HOBCB). As its molecular structure suggests, 4-HOBCB can be used in the performance enhancement of a number of important engineering thermoplastics, such as polyethersulfones (PES), polyetherketones (PEK), polycarbonates (PC), whose syntheses require phenolic starting materials. For example, the network polymers derived from bisphenol-A polycarbonate terminated with 4-HOBCB have shown excellent solvent and ignition resistance, as well as good toughness over a broad range of crosslink densities. It has also been shown that systems derived from AB-benzocyclobutene (BCB)-maleimide (MI) monomers were easy to process and the resulting matrix maerials were much tougher than other advanced thermosets for aerospace applications. 4-HOBCB was an important ingredient for a number of these AB-BCB-MI monomers. Another important advantage of 4-HOBCB over 4-AMBCB is its amenability to a large-scale, environmentally benign synthesis process using a biocatalyst in an aqueous medium.

4-HOBCB was first prepared from bis(4-aminobenzocyclobutene) sulfate under diazotization conditions. It can also be synthesized from benzocyclobutene-4carboxaldehyde via a modified Baeyer-Villiger reaction using permonophosphoric acid prepared from 70% hydrogen peroxide solution and phosphorus pentoxide, or from copper-catalyzed nucleophilic substitution reaction of an alkali hydroxide and 4bromobenzocyclobutene. Additionally, it has been demonstrated that benzocyclobutene can be enzymatically dioxygenated to an intermediate diol which undergoes facile dehydration to 4-HOBCB.

We have discovered a novel method for the preparation of 4-HOBCB. We have also prepared a new substituted benzocyclobutene compound.

It is therefore an object of the present invention to provide a novel method for the preparation of 4-HOBCB.

It is a further object of the present invention to provide a new substituted benzocyclobutene compound.

Other objects and advantages of the present invention will be apparent to those skilled in the art.

SUMMARY OF THE INVENTION

In accordance with the present invention, we have discovered that 4-HOBCB can be prepared by the demethylation of 4-methoxybenzocyclobutene by aluminum iodide. We have also prepared a new compound 4-trimethylsiloxybenzocyclobutene.

DETAILED DESCRIPTION OF THE INVENTION

4-HOBCB is prepared starting from commercially available 3-methoxyphenylacetic acid, as shown by the following reaction scheme:

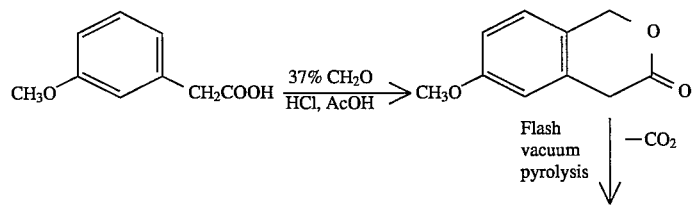

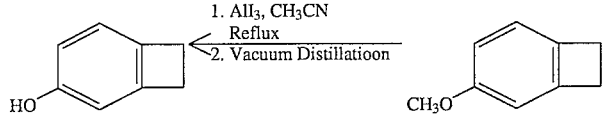

Preparation of 4-methoxybenzocyclobutene from 3-methoxyphenylacetic acid is a known procedure. Preparation of 4-HOBCB by the demethylation of 4-methoxybenzocyclobutene in the presence of aluminum iodide is described in the Examples which follow. Briefly, the procedure comprises heating 4-methoxybenzocyclobutene in a solvent such as acetonitrile in the presence of freshly prepared aluminum iodide, under reflux conditions for a time ranging from about 1 to 10 hours. The crude product is then recovered and purified according to standard laboratory practices.

4-Trimethylsiloxybenzocyclobutene is prepared from 4-HOBCB as shown by the following reaction:

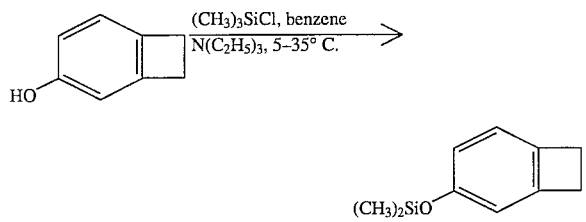

Briefly, the process comprises reacting 4-HOBCB with chlorotrimethylsilane in the presence of triethylamine, in a suitable solvent such as benzene, under anhydrous conditions. The reaction is preferably carried out at a temperature below ambient temperature, e.g., at about 0° to 10° C., for about 2 to 20 hours.

The following examples illustrate the invention:

EXAMPLE I

Reaction of 4-methoxybenzocyclobutene with Aluminum Iodide

Into a 100 ml round-bottomed flask were placed small, torn aluminum foils (0.65 g., 24.08 mmol.) and iodine crystals (9.36 g, 36.88 mmol.), and 20 ml of dry acetonitrile was added subsequently. The resultant mixture was heated under nitrogen to gentle reflux. The aluminum foils disappeared as a dark, heterogeneous mixture containing yellow precipitates formed. The mixture was refluxed for about 3 hours and allowed to cool to room temperature. 4-Methoxybenzocyclobutene (3.00 g., 2.36 mmol.) (obtained from Daychem Labs Inc., Dayton, Ohio), in 10 ml of acetonitrile was added rapidly to the freshly prepared $AlI_3/CH_3CN$ mixture. Heating was resumed and the reaction mixture was refluxed for an additional 5 hours. The final reaction mixture was lighter in color (brown) and containing more precipitates than the fresh $AlI_3/CH_3CN$ mixture. The cooled, heterogeneous mixture was poured into a 500 ml separatory funnel containing 300 ml of distilled water, and extracted thrice with methylene chloride (100 ml, and 2×50 ml.). The combined, dark $CH_2Cl_2$ extract was washed with 15% aqueous sodium hydrosulfite solution until the $CH_2Cl_1$ layer was very light yellow, which was subsequently dried over $MgSO_4$. Thin-layer chromatography of the final $CH_2Cl_2$ solution showed only one spot and its $R_f$ was lower than that of the starting 4-methoxybenzocyclobutene, when eluted by 1:1 ethyl acetate/hexane. Complete removal of the solvent from the $CH_2Cl_2$ solution via rotary evaporation provided the crude product as a yellow oil. Yield: 2.58 g. Mass spectrum of the crude product suggested, besides the major product, 4-HOBCB, the presence of very minor amounts of ring-opened side-product(s), 2-(3-hydroxyphenyl)-1-iodoethane and/or 2-(4-hydroxyphenyl)-1-iodoethane ($M^+$, m/z= 248).

In one preparation, a low melting, yellowish solid (60% yield) was obtained after the crude yellow oil was placed at 0.3 mm Hg at room temperature overnight. The crude product (3.20 g) could be purified by short-path vacuum distillation to a white crystalline solid (1.20 g.; b.p. 45°–50° C. at 0.30 mm Hg; m.p. 45°–46° C). Anal. Calc. for $C_8H_8O$: C, 79.96%; H, 6.72%. Found: C, 79.95%; H.6.95%.

Mass spectrum: ($M^+$, m/z 120, relative abundance 100%).

Infra-red spectrum: (KBr; $cm^{-1}$): 3245 (OH stretch), 2972, 2931 (benzocyclobutenyl $CH_2$ stretch), 1599 (aromatic C=C stretch), 1460 ($CH_2$ deformation) and 1245 ($sp^2C$—O stretch).

$^1$HNMR: (270 MHz, $CDCl_3$, δ in ppm from internal TMS): 3.02 (singlet, alicyclic protons); 5.47 (singlet, slightly broad, OH); 6.58, 6.59 (doublet, $J_{bc}$=2.2 Hz; aromatic proton ortho to both OH and alicyclic groups); 6.63, 6.64 6.66, 6.67 (doublet of doublet, $J_{bc}$=2.2 Hz and $J_{ab}$=8.05 Hz; aromatic proton ortho to alicyclic group and meta to OH group). 6.82, 6.85 (doublet, $J_{ab}$=8.05 Hz, aromatic proton ortho to OH group and meta to alicyclic group).

$^{13}$CNMR (270 MHz, $CDCl_3$, δ in ppm from internal TMS): 28.57.($sp^3$ C, commutable), 28.80 ($sp^3$C, commutable); 110.34 ($sp^2$ C meta to $sp^2$C—OH and ortho to $sp^2$C cyclobutene); 114.03 ($sp^2$C ortho to $sp^2$C—OH and ortho to $sp^2$C cyclobutene); 123.47 ($sp^2$C ortho to $sp^2$C—OH and meta to $sp^2$C cyclobutene); 137.41 ($sp^2$C cyclobutene para to $sp^2$C—OH); 146.68 ($sp^2$C cyclobutene meta to $sp^2$C—OH), 154.74 ($sp^2$C attached to OH).

COMPARATIVE EXAMPLE I

Reaction of 4-Hyroxybenzocyclobutene with Iodotrimethylsilane

4-Methoxybenzocyclobutene (3.00 g, 22.36 mmol.) and sodium iodide (3.52 g.) were placed in a 200 ml round-bottomed flask followed by addition of 40 ml acetonitrile. NaI dissolved readily. To the resultant clear and colorless solution was added slowly chlorotrimethylsilane. Immediately, the reaction mixture became yellow with concomitant precipitation of fine powder of sodium chloride. The reaction mixture was stirred at room temperature under nitrogen overnight. GC/MS indicated >95% of 4-methoxybenzocyclobutene remained in the reaction mixture.

COMPARATIVE EXAMPLE II

Reaction of 4-Hydroxybenzocyclobutene with Boron Tribromide

4-Methoxybenzocyclobutene (4.0 g., 29.81 mmol) was placed in a 100 ml, three necked round-bottomed flask equipped with a septum, reflux condenser with nitrogen adaptor, and a thermometer. Dry methylene chloride (20 ml) was added to form a clear and colorless solution. Under a nitrogen flow, 1 M $BBr_3/CH_2Cl_2$ solution (40 ml) was added slowly at room temperature via a hypodermic syringe. Immediately, the reaction mixture became deep red (still homogeneous) with the internal temperature rising to ca. 45° C. Addition of $BBr_3/CH_2Cl_2$ solution was then carried out at such rate that the reaction temperature was kept below 35° C. The final deep red, homogeneous reaction mixture was stirred at room temperature under nitrogen for 14 hr. The now dark brown and homogeneous solution was poured into a 1-liter separatory funnel containing about 300 ml of water. The products was extracted into methylene chloride (2×50 ml +1×25 ml). The combined extract was dried over $MgSO_4$ and filtered. Removal of the the solvent via rotary evaporation led to the isolation of a green oil. Thin layer chromatography of the methylene chloride extract indicated all 4-methoxybenzocyclobutene has been consumed. Proton nuclear magnetic resonance run of the green oil indicated that the aliphatic ring of benzocyclobutene has been ruptured, and mass spectrum suggested the product to be 2-(3-hydroxyphenyl)-1-bromoethane and / or 2-(4-hydroxyphenyl)-1-bromoethane.

EXAMPLE II

Synthesis of 4-trimethylsiloxybenzocyclobutene

To 3.14g (0,026 moles) of 4-hydroxybenzocyclobutene taken up in 10 ml anhydrous benzene was added 2.64 g of triethylamine in a nitrogen-swept three-necked flask. Chlorotrimethylsilane (4.16 g, 0,038 moles) in 5 ml benzene was added at 15° C. over a period of 15 minutes. The mixture was was kept at 20° C. overnight and was refluxed for about two hours to complete the reaction. The precipitated triethylamine hydrochloride was filtered off under a nitrogen blanket and more benzene (25 ml) was filtered through the solid to extract all the product. A pale yellow oil was obtained after removing the solvents by distillation under nitrogen pressure. The residual volatiles were removed and the crude product was vacuum distilled (65°–67° C., 0.5 mm Hg) to collect a colorless oil (1.2 g. 24% yield). Anal. Calc.: C, 68.69%; H, 8.38%. Found: C, 69.34%; H, 8.33%

A larger batch of 4-trimethylsiloxybenzocyclobutene was synthesized from 6.56 gms of 4-hydroxybenzocyclobutene and 5.54 gms of triethylamine, taken up in 15 ml anhydrous benzene followed by the addition of a nearly three molar excess of chlorotrimethylsilane (20 ml in 15 ml dry benzene) to the reaction mixture maintained at 5° C. An instant white precipitation of triethylamine hydrochloride was observed. The solution was allowed to warm up on its own to 15° C. in about 5 hours and the reaction mixture was kept stirred overnight, It was warmed to 40° C. and maintained for about three hours. The reaction mixture was cooled and the isolation of the product was done exactly as described before. The weight of the light yellow oil (crude) was 7.93 g, 76% yield. Total amount of the colorless oil obtained from vacuum distillation was 7.07 grams. Anal. Calc.: C, 68.69%; H, 8.38%. Found: C, 69.15%; H, 8.44%.

Mass spectrum: ($M^+$, m/z 192, relative abundance 100%).

Infra-red spectrum: (neat, $cm^{-1}$): 3080 (aromatic CH), 2967 ($CH_3$ stretch), 2931 (benzocyclobutenyl $CH_2$ stretch), 1594 (aromatic C=C), 1471 ($CH_2$ deformation), 1270 (benzocyclobutenyloxy stretch) and 951 (Ar-$OSiMe_3$).

$^1HNMR$ ($CDCl_3$, no TMS, ppm): 0.28 (s, 9H, -$OSiMe_3$), 3.12 (s, 4H, benzocyclobutenyl $CH_2$), 6.61, 6.62 (d, 1H, aromatic proton ortho to both $OSiMe_3$ and alicyclic group), 6.69–6.72 (dd, 1H, aromatic proton ortho to alicyclic group and meta to $OSiMe_3$) and 6.91, 6.94 (d, 1H, aromatic proton ortho to $OSiMe_3$ group and meta to alicyclic group).

$^{13}CNMR$ ($CDCl_3$, no TMS, 77 ppm for $CDCl_3$ as reference): 0.18–0.64 ($OSiMe_3$ carbons), 28.68, 28.92 (benzocyclobutenyl $CH_2$), 114.95 ($sp^2$ C meta to C-$OSiMe_3$ and ortho to alicyclic), 119.84 ($sp^2$ C ortho to C-$OSiMe_3$ and ortho to alicyclic), 123.42 ($sp^2$ C ortho to C-$OSiMe_3$ and meta to alicyclic), 138.16 ($sp^2$ C cyclobutene para to C-$OSiMe_3$), 146.34 ($sp^2$ C cyclobutene meta to C-$OSiMe_3$) and 154.40 ($sp^2$ C-$OSiMe_3$).

Various modifications may be made in the instant invention without departing from the spirit and scope of the appended claims.

We claim:

1. A method for the preparation of 4-hydroxybenzocyclobutene which comprises heating 4-methoxybenzocyclobutene in acetonitrile in the presence of freshly prepared aluminum iodide, under reflux conditions for about 1 to 10 hours, and recovering and purifying the resulting crude product.

2. A method for the preparation of 4-trimethylsiloxybenzocyclobutene which comprises reacting 4-hydroxybenzocyclobutene with chlorotrimethylsilane in the presence of triethylamine.

3. 4-Trimethylsiloxybenzocyclobutene.

\* \* \* \* \*